(12) United States Patent
Park et al.

(10) Patent No.: US 8,963,564 B2
(45) Date of Patent: Feb. 24, 2015

(54) SALINITY MEASURING APPARATUS

(75) Inventors: Nam Ju Park, Suwon-si (KR); Jeong Su Han, Suwon-si (KR); Hyo Sang Lee, Osan-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 749 days.

(21) Appl. No.: 13/067,650

(22) Filed: Jun. 16, 2011

(65) Prior Publication Data

US 2011/0316564 A1 Dec. 29, 2011

(30) Foreign Application Priority Data

Jun. 24, 2010 (KR) .................. 10-2010-0059910

(51) Int. Cl.
G01R 27/26 (2006.01)
G01N 27/06 (2006.01)
G01N 33/02 (2006.01)
G01R 27/02 (2006.01)
(Continued)

(52) U.S. Cl.
CPC ............. *G01N 27/06* (2013.01); *G01N 33/02* (2013.01); *G01R 27/02* (2013.01); *G01R 27/22* (2013.01); *G01N 27/221* (2013.01); *G01N 33/2852* (2013.01); *G01N 27/223* (2013.01)
USPC ........................................ 324/672

(58) Field of Classification Search
CPC ..... G01N 33/18; G01N 33/182; G01N 27/06; G01N 27/223; G01V 1/38; G01V 1/46; G01R 27/22; G01R 27/2635; B01L 2300/0645; G05B 23/02
USPC ....................................... 324/672
See application file for complete search history.

(56) References Cited

U.S. PATENT DOCUMENTS 2,173,233 A * 9/1939 Lieneweg et al. ............. 324/443
3,460,032 A 8/1969 Bement et al.
(Continued)

FOREIGN PATENT DOCUMENTS

EP 0010823 A1 5/1980
EP 0582329 A1 * 2/1994 ............. G01R 27/22
(Continued)

OTHER PUBLICATIONS

European Search Report dated Sep. 30, 2011 issued in corresponding European Patent Application No. 11170847.5.
(Continued)

*Primary Examiner* — Patrick Assouad
*Assistant Examiner* — Sean Curtis
(74) *Attorney, Agent, or Firm* — Staas & Halsey LLP

(57) ABSTRACT

A salinity measuring apparatus to determine salinity of food includes a salinity sensing unit including a pair of measuring electrodes and a capacitor, a switching unit to switch a voltage of the capacitor of the salinity sensing unit, and a control unit to provide a pulse signal with a constant frequency to the switching unit and to determine the salinity of the food which is in contact with the measuring electrodes of the salinity sensing unit based on when the voltage of the capacitor reaches a reference voltage. By providing the pulse signal with the constant frequency to the switching unit, it is possible to minimize the internal impedance variation of the capacitor and to more accurately measure the salinity of the food. Since a period when the voltage of the capacitor is substantially "0" is present, it is possible to minimize accumulation of ions in the measuring electrodes.

18 Claims, 12 Drawing Sheets

(51) Int. Cl.
*G01R 27/22* (2006.01)
*G01N 27/22* (2006.01)
*G01N 33/28* (2006.01)

(56) References Cited

U.S. PATENT DOCUMENTS

| | | | | |
|---|---|---|---|---|
| 3,565,642 | A * | 2/1971 | Hirsch | 99/358 |
| 3,757,205 | A * | 9/1973 | Dauphinee | 324/444 |
| 4,015,195 | A * | 3/1977 | Hoyer et al. | 324/323 |
| 4,092,629 | A * | 5/1978 | Siems et al. | 367/79 |
| 4,656,427 | A * | 4/1987 | Dauphinee | 324/444 |
| 4,754,839 | A * | 7/1988 | Gold et al. | 181/102 |
| 4,823,087 | A * | 4/1989 | Sugimori | 324/441 |
| 4,833,413 | A * | 5/1989 | Head | 324/449 |
| 5,657,238 | A | 8/1997 | Lindeboom | |
| 5,861,758 | A * | 1/1999 | Berberich | 324/694 |
| 5,929,689 | A * | 7/1999 | Wall | 327/362 |
| 6,107,924 | A * | 8/2000 | Kasai et al. | 340/627 |
| 6,837,182 | B2 * | 1/2005 | Leblanc | 119/220 |
| 7,135,870 | B2 * | 11/2006 | Mohajer et al. | 324/639 |
| 7,408,364 | B1 * | 8/2008 | Campbell | 324/644 |
| 7,482,820 | B1 * | 1/2009 | Campbell | 324/644 |
| 7,535,237 | B1 * | 5/2009 | Campbell | 324/644 |
| 8,350,571 | B2 * | 1/2013 | Son | 324/441 |
| 2003/0051674 | A1 * | 3/2003 | Leblanc | 119/220 |
| 2007/0215613 | A1 * | 9/2007 | Kinzer | 219/764 |
| 2008/0211521 | A1 * | 9/2008 | Lock | 324/696 |
| 2009/0267617 | A1 * | 10/2009 | Seyfi et al. | 324/655 |
| 2010/0254218 | A1 * | 10/2010 | Dorovsky et al. | 367/38 |
| 2011/0140704 | A1 * | 6/2011 | Son | 324/441 |

FOREIGN PATENT DOCUMENTS

| | | | |
|---|---|---|---|
| EP | 0582329 A1 | 2/1994 | |
| EP | 0 582 329 A1 * | 9/1994 | G01R 27/22 |
| EP | 1128180 A2 | 8/2001 | |
| EP | 1128180 A3 | 8/2001 | |
| IT | EP0582329 A1 * | 9/1994 | G01R 27/22 |
| JP | 2002-005862 | 1/2002 | |
| JP | 2002-5862 | 1/2002 | |
| KR | 10-2008-0068362 | 7/2008 | |

OTHER PUBLICATIONS

Paolo Bruschi et al. "A Current-Mode, Dual Slope, Integrated Capacitance-to-Pulse Duration Converter", IEEE Journal of Solid-State Circuits, vol. 42. No. 9, Sep. 2007, pp. 1884-1891.

Andrea De Marcellis et al. "A CMOS Integrable Oscillator-Based Front End for High-Dynamic-Range Resistive Sensors", IEEE Transactions on Instrumentation and Measurement, vol. 57. No. 8, Aug. 2008, pp. 1596-1604.

Zeljko lgnjatovic et al. "An Interface Circuit for Measuring Capacitance Changes Based Upon Capacitance-to-Duty Cycle (CDC) Converter", IEEE Sensors Journal, vol. 5. No. 3, Jun. 2005, pp. 403-410.

Julia Hsin-Lin Lu et al. "A Low-Power, Wide-Dynamic-Range Semi-Digital Universal Sensor Readout Circuit Using Pulsewidth Modulation", IEEE Sensors Journal, vol. 11. No. 5, May 2011, pp. 1134-1144.

* cited by examiner

SALINITY MEASURING APPARATUS

CROSS-REFERENCE TO RELATED APPLICATIONS

This application claims the benefit of Korean Patent Application No. 2010-0059910, filed on Jun. 24, 2010 in the Korean Intellectual Property Office, the disclosure of which is incorporated herein by reference.

BACKGROUND

1. Field

Embodiments relate to a salinity measuring apparatus to measure salinity of a solution.

2. Description of the Related Art

Kimchi is a traditional Korean food produced through fermentation. The rate of fermentation of Kimchi varies according to temperature and salinity.

The rate of fermentation of Kimchi is increased if temperature is high and salinity is low and is decreased if temperature is low and salinity is high.

Accordingly, in order to determine an appropriate Kimchi fermentation period, the internal temperature of a Kimchi storage chamber and salinity of Kimchi need to be measured.

The existing salinity measuring apparatus includes a salinity sensing unit having a pair of measuring electrodes and a capacitor, and a switching unit operating according to an output signal of the salinity sensing unit so as to switch a voltage supplied to the salinity sensing unit. Such a salinity measuring apparatus converts the voltage of the capacitor changed according to salinity into a frequency using predetermined upper and lower limit values and measures salinity according to the frequency.

However, in the existing salinity measuring apparatus, since the frequency is changed whenever salinity is measured, a measurement error may occur due to an internal impedance variation of the capacitor. Thus, it is difficult to accurately measure the salinity of food.

In addition, in the existing salinity measuring apparatus, when salinity is consecutively measured, a DC voltage component is partially supplied to the measuring electrodes, such that, over time, ions are accumulated in the measuring electrodes. Thus, electrical conductivity is lowered with over time. Accordingly, even when food having the same salinity is measured, since electrical conductivity is lowered due to ions accumulated in the measuring electrodes, the measured salinity may be changed whenever the salinity is measured. In addition, salinity lower than actual salinity may be measured and thus reliability of measured data may be reduced.

In addition, in the existing salinity measuring apparatus, since an oscillation frequency is increased as the salinity of the food is increased, switching loss of a self-oscillating circuit is generated.

SUMMARY

Therefore, it is an aspect to provide a salinity measuring apparatus capable of accurately, reliably and effectively measuring the salinity of food.

Additional aspects will be set forth in part in the description which follows and, in part, will be apparent from the description, or may be learned by practice of the invention.

In accordance with one aspect, there is provided a salinity measuring apparatus to determine salinity of food, the salinity measuring apparatus including: a salinity sensing unit including a pair of measuring electrodes and a capacitor; a switching unit to switch a voltage of the capacitor of the salinity sensing unit; and a control unit to provide a pulse signal with a constant frequency to the switching unit and to determine the salinity of the food which is in contact with the measuring electrodes of the salinity sensing unit based on when the voltage of the capacitor reaches a reference voltage.

In the salinity sensing unit, the capacitor may be connected to any one of the measuring electrodes in series.

The salinity sensing unit may further include a resistor connected between the measuring electrodes in parallel.

The salinity measuring apparatus may further include a memory unit to store a salinity value varying according to when the voltage of the capacitor reaches the reference voltage.

The salinity measuring apparatus may further include a comparison unit to compare the voltage of the capacitor of the salinity sensing unit with the reference voltage and to output a high-level signal or a low-level signal according to the comparison result, and the control unit may determine when the voltage of the capacitor reaches the reference voltage based on a variation in output signal of the comparison unit.

The salinity measuring apparatus may further include an AD converter connected to the capacitor so as to convert an analog voltage signal of the capacitor into a digital signal, and the time when the voltage of the capacitor reaches the reference voltage may be determined according to the digital signal converted by the AD converter.

The control unit may control the switching unit such that the capacitor is discharged when the voltage of the capacitor reaches the reference voltage.

The period of the pulse signal may include a period when the voltage of the capacitor is substantially 0.

The salinity measuring apparatus may further include a discharging unit connected to one side of the capacitor of the salinity sensing unit so as to discharge the capacitor.

The operation of the discharging unit may interlock with a discharging operation of the switching unit.

In accordance with another aspect, there is provided a salinity measuring apparatus including: a salinity sensing unit including a pair of measuring electrodes and a capacitor; a switching unit to switch a voltage of the capacitor of the salinity sensing unit; and a control unit to provide a pulse signal with a constant frequency to the switching unit, to determine a duty ratio of the pulse signal when the voltage of the capacitor reaches the reference voltage, and to determine salinity of food which is in contact with the measuring electrodes of the salinity sensing unit according to the determined duty ratio.

The salinity measuring apparatus may further include a memory unit to store a salinity value corresponding to the duty ratio.

The salinity measuring apparatus may further include a comparison unit to compare the voltage of the capacitor of the salinity sensing unit with the reference voltage and to output a high-level signal or a low-level signal according to the comparison result, and the control unit may determine a time from when the pulse signal is output to the switching unit to when the output signal of the comparison unit is changed, as the duty ratio of the pulse signal.

The control unit may control the switching unit such that the capacitor is discharged when the voltage of the capacitor reaches the reference voltage.

The period of the pulse signal may include a period when the voltage of the capacitor is substantially 0.

The salinity measuring apparatus may further include a discharging unit connected to one side of the capacitor of the salinity sensing unit so as to discharge the capacitor.

The operation of the discharging unit may interlock with a discharging operation of the switching unit.

In accordance with another aspect, there is provided a salinity measuring apparatus including: a salinity sensing unit including a pair of measuring electrodes and a capacitor; a switching unit switched to charge or discharge the capacitor of the salinity sensing unit; and a control unit to control the switching unit so as to charge the capacitor and to control the switching unit so as to discharge the capacitor when the voltage of the capacitor reaches a reference voltage.

The salinity measuring apparatus may further include a comparison unit to compare the voltage of the capacitor of the salinity sensing unit with the reference voltage and to output a high-level signal or a low-level signal according to the comparison result, and the control unit may determine whether or not the voltage of the capacitor reaches the reference voltage based on variation in an output signal of the comparison unit.

The period of the pulse signal may include a period when the voltage of the capacitor is substantially 0.

In accordance with a further aspect, there is provided a salinity measuring apparatus including: a salinity sensing unit including a pair of measuring electrodes and a capacitor; a switching unit to switch a voltage applied to the salinity sensing unit; and a control unit to provide a pulse signal with a constant frequency to the switching unit, to change a duty ratio of the pulse signal based on when the voltage of the capacitor reaches a reference voltage, and to determine salinity of food which is in contact with the measuring electrodes of the salinity sensing unit.

According to the embodiments, by providing the pulse signal with the constant frequency to the switching unit, it is possible to minimize the internal impedance variation of the capacitor and to more accurately measure the salinity of the food.

In addition, according to the embodiments, since a period when the voltage of the capacitor is substantially "0" is present, it is possible to minimize accumulation of ions in the measuring electrodes and to reliably measure the salinity of the food.

According to the embodiments, since the frequency of the pulse signal provided to the switching unit is only constant, it is possible to reduce the frequency of the pulse signal, to reduce the switching loss of the switching unit, and to reduce energy consumption.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
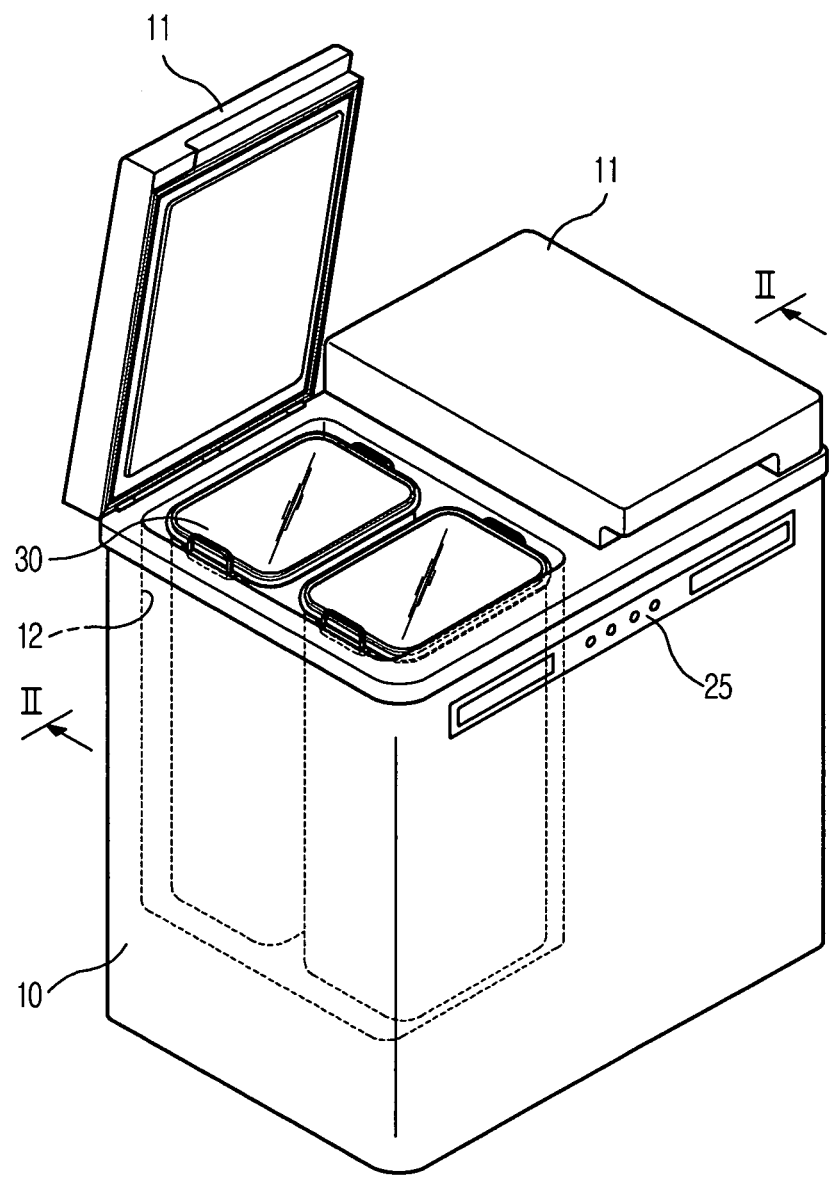
FIG. 1 is a perspective view of a Kimchi refrigerator to which a salinity measuring apparatus according to an embodiment is applied.

Reference will now be made in detail to the embodiments, examples of which are illustrated in the accompanying drawings, wherein like reference numerals refer to like elements throughout.

Figure 2:
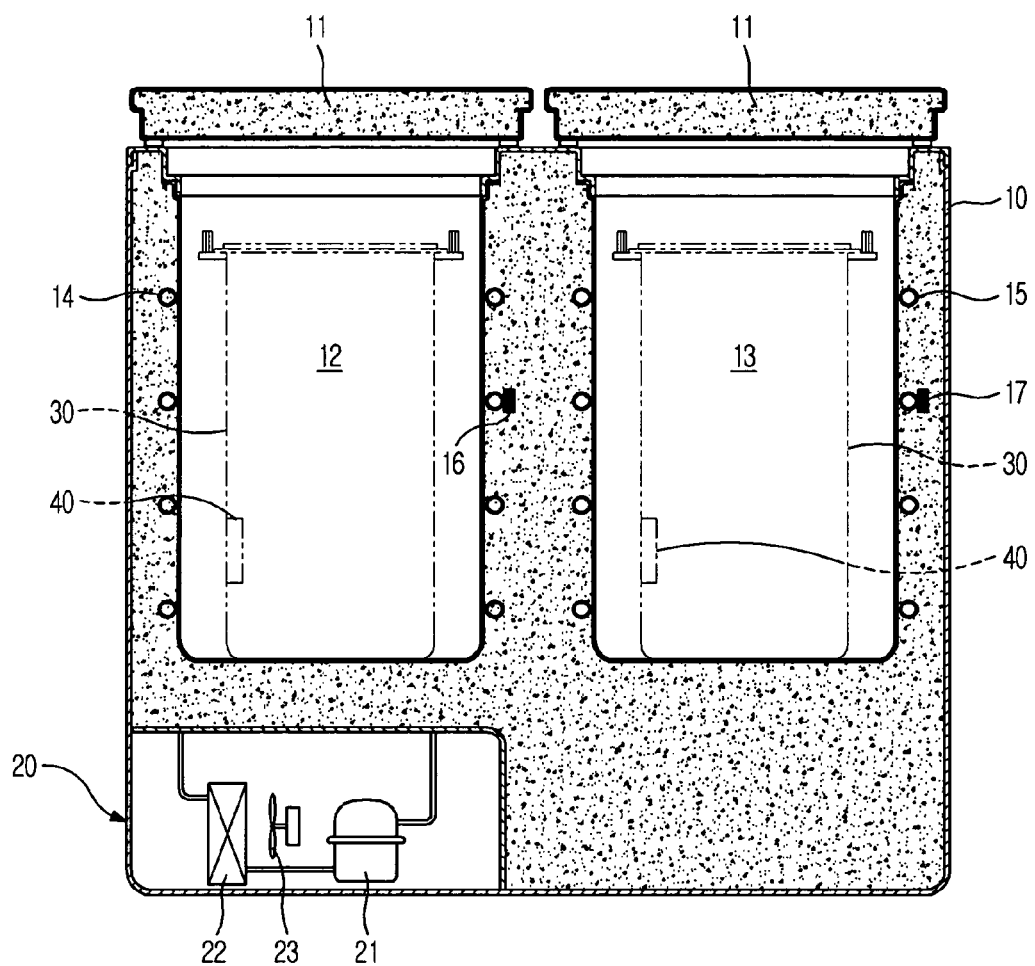
FIG. 2 is a cross-sectional view taken along line of the Kimchi refrigerator shown in FIG. 1.

FIG. 1 is a perspective view of a Kimchi refrigerator to which a salinity measuring apparatus according to an embodiment is applied. FIG. 2 is a cross-sectional view taken along line II-II of the Kimchi refrigerator shown in FIG. 1.

As shown in FIGS. 1 and 2, the Kimchi refrigerator, to which the salinity measuring apparatus according to the embodiment of the present invention is applied, includes a main body 10.

A function selection unit 25 is provided on an upper side of a front surface of the main body 10.

A first storage chamber 12 and a second storage chamber 13 are formed in the main body 10.

Doors 11 to open or close the first storage chamber 12 and the second storage chamber 13 are hinge-coupled to an upper side of the main body 10.

The first storage chamber 12 and the second storage chamber 13 are separated by a partition.

An insulator to maintain the temperatures of the first storage chamber 12 and the second storage chamber 13 is filled between outer surfaces of the first storage chamber 12 and the second storage chamber 13.

A first evaporator 14 to perform a heat exchange operation and a first temperature sensor 16 to detect a surface temperature of the first evaporator 14 in order to sense the temperature of the first storage chamber 12 are provided on the outer circumference of the first storage chamber 12.

A second evaporator 15 to perform a heat exchange operation and a second temperature sensor 17 to detect a surface temperature of the second evaporator 15 in order to sense the temperature of the second storage chamber 13 are provided on the outer circumference of the second storage chamber 13.

A machine room 20 including cooling devices is provided below the first storage chamber 12 and the second storage chamber 13.

In the machine room 20, a compressor 21 to compress refrigerant, a condenser to condense the refrigerant compressed by the compressor 21, and a fan 23 provided on one side of the condenser 22 to force air to the condenser 22 are provided.

A storage container 30 to store Kimchi is received in each of the first storage chamber 12 and the second storage chamber 13. In the storage container 30, a salinity measuring apparatus 40 to measure the salinity of food stored in the storage container, such as Kimchi, is mounted. Here, the salinity measuring apparatus 40 is provided inside the storage container 30 such that measuring electrodes are in contact with the liquid of the food stored in the storage container 30, thereby measuring salinity.

The salinity measuring apparatus 40 has a pair of measuring electrodes spaced apart from each other with a predetermined gap therebetween. The measuring electrodes are provided so as to be in contact with the liquid of the food stored in the storage chamber.

For example, the salinity measuring apparatus 40 applies a voltage to the pair of measuring electrodes so as to measure electrical conductivity between the measuring electrodes and to measure the salinity of the food based on the electric conductivity. In this case, as the electric conductivity is increased, the salinity of Kimchi is increased and as the electric conductivity is decreased, the salinity of Kimchi is decreased.

The Kimchi refrigerator having the above-described configuration sets a fermentation time or a fermentation temperature according to a fermentation mode or a ripening step determined by user selection according to the salinity of the food measured by the salinity measuring apparatus 40. Thus, an appropriate fermentation period can be determined according to the salinity of Kimchi such that the food is fermented to a desired degree regardless of the salinity of the food.

Hereinafter, the detailed configuration of the salinity measuring apparatus according to the embodiment of the present invention will be described.

Figure 3:
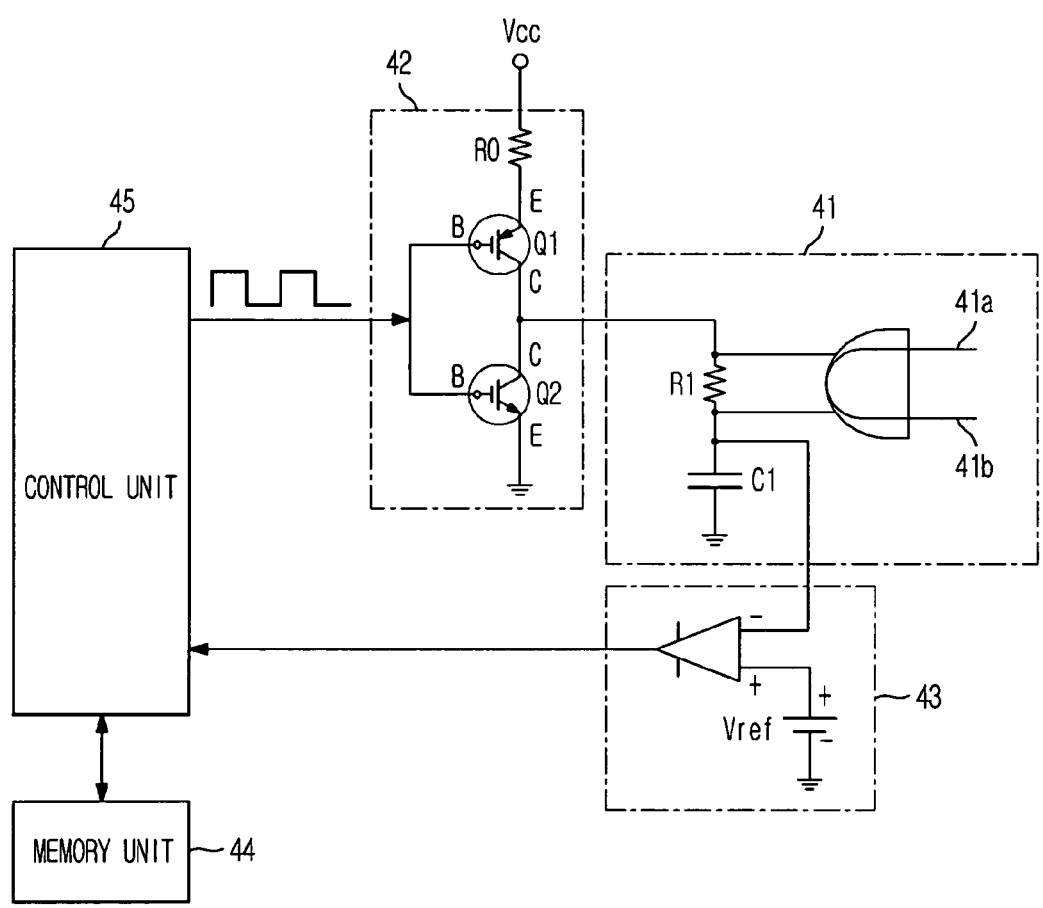
FIG. 3 is a block diagram of a salinity measuring apparatus according to an embodiment.

FIG. 3 is a block diagram of a salinity measuring apparatus according to an embodiment.

As shown in FIG. 3, the salinity measuring apparatus 40 according to the embodiment includes a salinity sensing unit 41, a switching unit 42, a comparison unit 43, a memory unit 44, and a control unit 45 to perform overall control.

The salinity sensing unit 41 includes a pair of measuring electrodes 41a and 41b, a resistor R1 and a capacitor C1.

The pair of measuring electrodes 41a and 41b includes the first electrode 41a and the second electrode 41b spaced apart from the first electrode 41 with a predetermined gap therebetween so as not to be in contact with the first electrode 41a. The first electrode 41a and the second electrode 41b are provided so as to be in contact with the liquid of the food stored in the storage chamber.

The capacitor C1 is connected to the second electrode 41b of the pair of measuring electrodes in series.

The first electrode 41a and the second electrode 41b are connected to both ends of the resistor R1. That is, the resistor R1 is connected between the first electrode 41a and the second electrode 41b in parallel.

The switching unit 42 supplies voltage to the salinity sensing unit 41 according to a pulse signal (e.g., a Pulse Width Modulation (PWM) signal) with a constant frequency, which is output from the control unit 45, so as to charge the capacitor C1 or to discharge the capacitor C1 to a ground side.

For example, the switching unit 42 includes two transistors Q1 and Q2. The two transistors Q1 and Q2 include the first switching element Q1 which is a PNP transistor and a second switching element Q2 which is an NPN transistor.

The base B of the first switching element Q1 and the base B of the second switching element Q2 are connected to each other.

The emitter E of the first switching element Q1 is connected to a source voltage Vcc.

The collector C of the second switching element Q2 is connected to the collector C of the first switching element Q1. The emitter E of the second switching element Q2 is grounded.

The resistor R1 and the capacitor C1 are connected in series between the collectors C of the first and second switching elements Q1 and Q2 and the ground.

The comparison unit 43 compares the voltage of the capacitor C1 of the salinity sensing unit 41 with a predetermined reference voltage Vref and outputs a high-level signal or a low-level signal to the control unit 45 according to the comparison result. When the control unit switches the first switching element Q1 of the switching unit 42 off upon sensing that a signal has changed from a high level to a low level.

The comparison unit 43 includes a comparator having a non-inverting input terminal (+) and an inverting input terminal (−). The inverting input terminal (−) of the comparison unit 43 is connected to a connection node between the second electrode 41b and the capacitor C1. The reference voltage Vref is input to the non-inverting input terminal (+) of the comparison unit 43.

Accordingly, the comparison unit 43 outputs a low-level signal when the voltage value input to the inverting input terminal (−) is higher than the reference voltage value Vref input to the non-inverting input terminal (+). In addition, the comparison unit 43 outputs a high-level signal when the voltage value input to the inverting input terminal (−) is lower than the reference voltage value Vref input to the non-inverting input terminal (+).

The control unit 45 includes a microcomputer. The control unit 45 outputs the pulse signal (e.g., the PWM signal) with the constant frequency to the switching unit 42 such that an AC voltage is supplied to the salinity sensing unit 41, and switches the first switching element Q1 of the switching unit 42 on so as to charge the capacitor C1 of the salinity sensing unit 41. At this time, the second switching element Q2 is switched off.

The control unit 45 controls the duty ratio of the PWM signal output to the switching unit 42 such that the capacitor C1 of the salinity sensing unit 41 is discharged, if the signal received from the comparison unit 43 is changed from the high-level signal to the low-level signal.

The first switching element Q1 of the switching unit 42 is switched off and the second switching element Q2 is switched on such that the capacitor C1 is discharged to the ground side through the second switching element Q2.

Meanwhile, the control unit 45 determines the salinity of the food which is in contact with the measuring electrodes 41a and 41b of the salinity sensing unit 41 based on a time when the voltage of the capacitor C1 reaches the reference voltage.

Salinity-time data is stored in the memory unit 44. The time value changed according to the salinity of the standard food measured by experiments is stored in the memory unit 44.

At this time, the time when the voltage of the capacitor C1 reaches the reference voltage is a time when the first switching element Q1 is switched on to a time when the first switching element Q1 is switched off, which corresponds to the duty ratio of the PWM signal. Thus, the control unit 45 may determine the salinity of the food by checking the duty ratio of the PWM signal. In this case, salinity-duty ratio data is stored in the memory unit 44.

Figure 4:
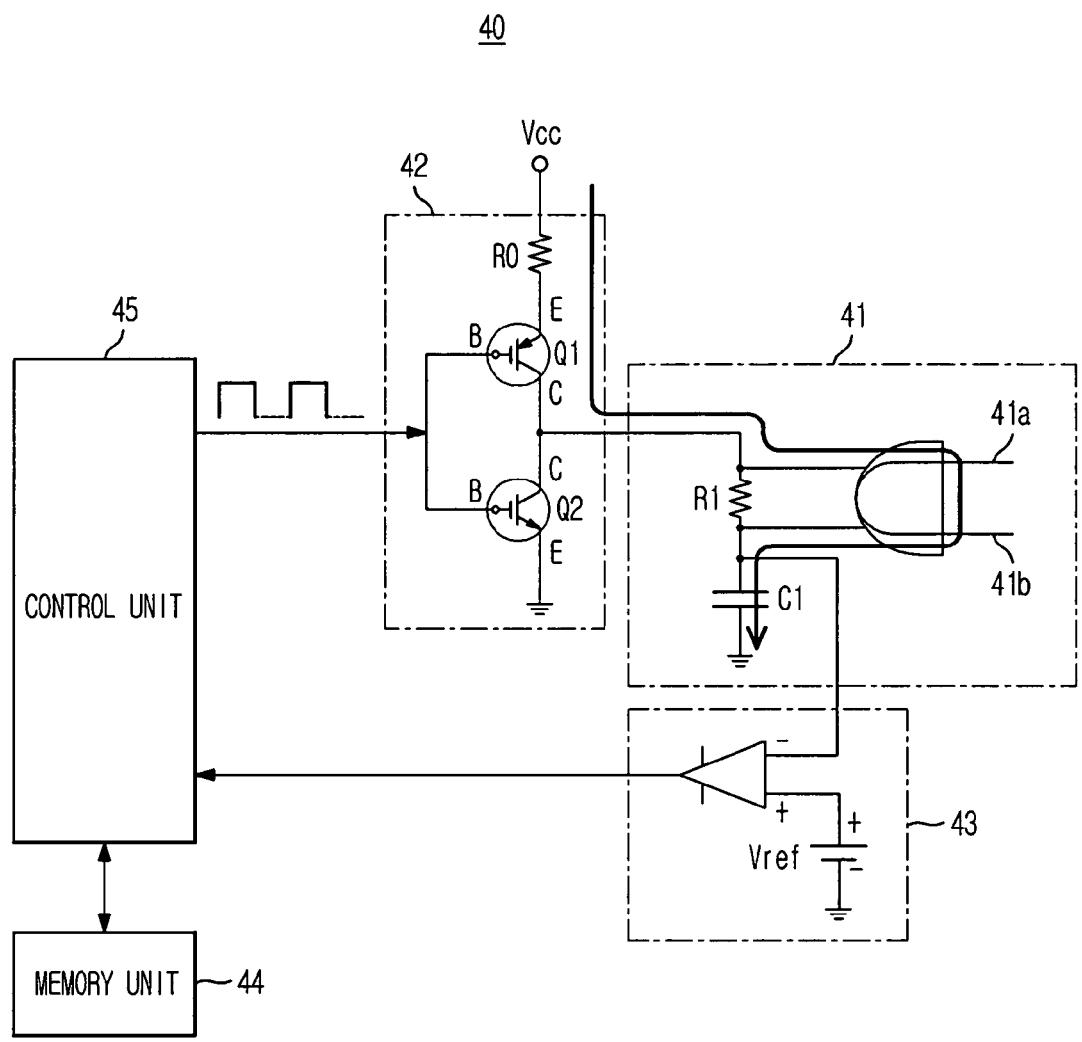
FIG. 4 is a diagram showing a state in which a voltage is applied to a capacitor through measuring electrodes of a salinity sensing unit shown in FIG. 3 so as to charge the capacitor.
Figure 5:
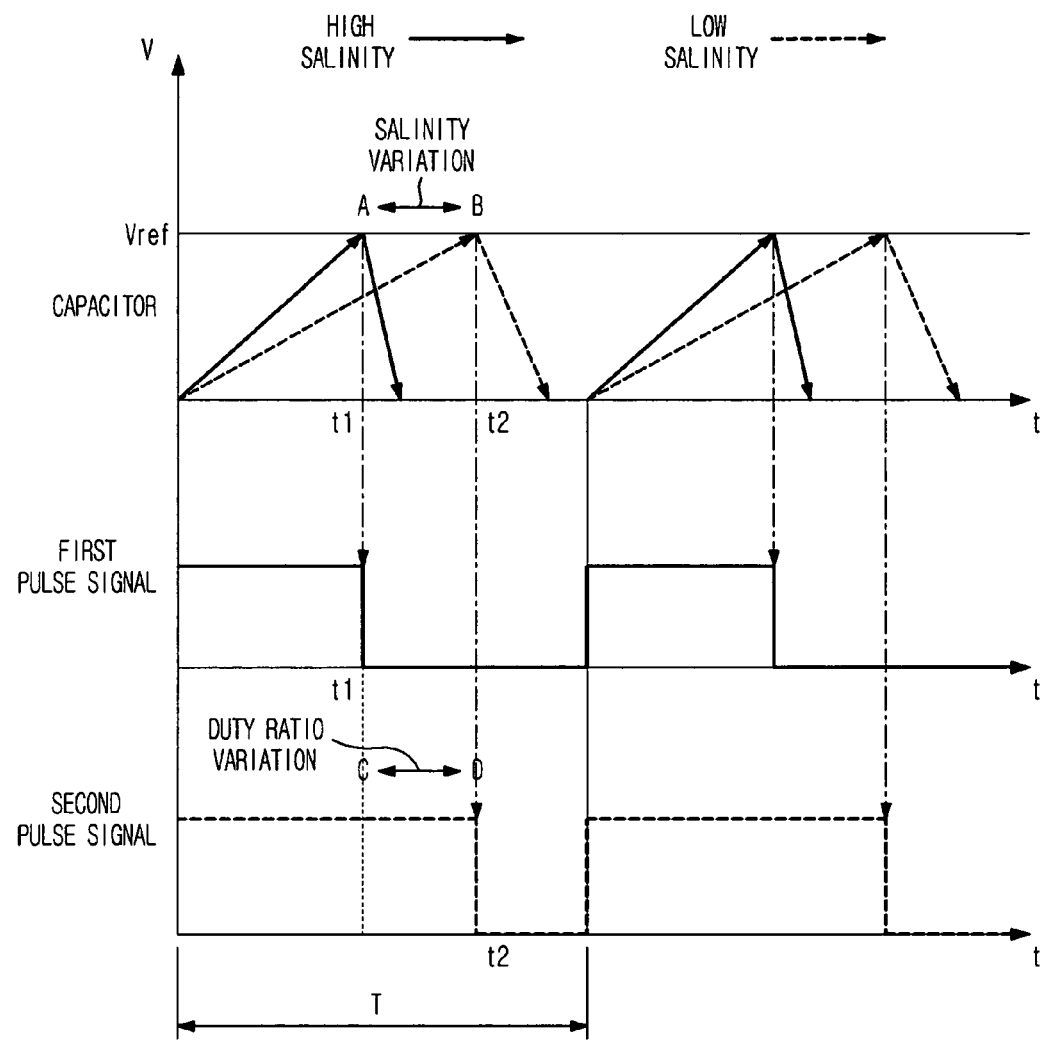
FIG. 5 is a timing chart illustrating a variation in time when the voltage of the capacitor reaches a reference voltage and a variation in duty ratio of a Pulse Width Modulation (PWM) signal according to a salinity variation, in the salinity measuring apparatus according to the embodiment.
Figure 6:
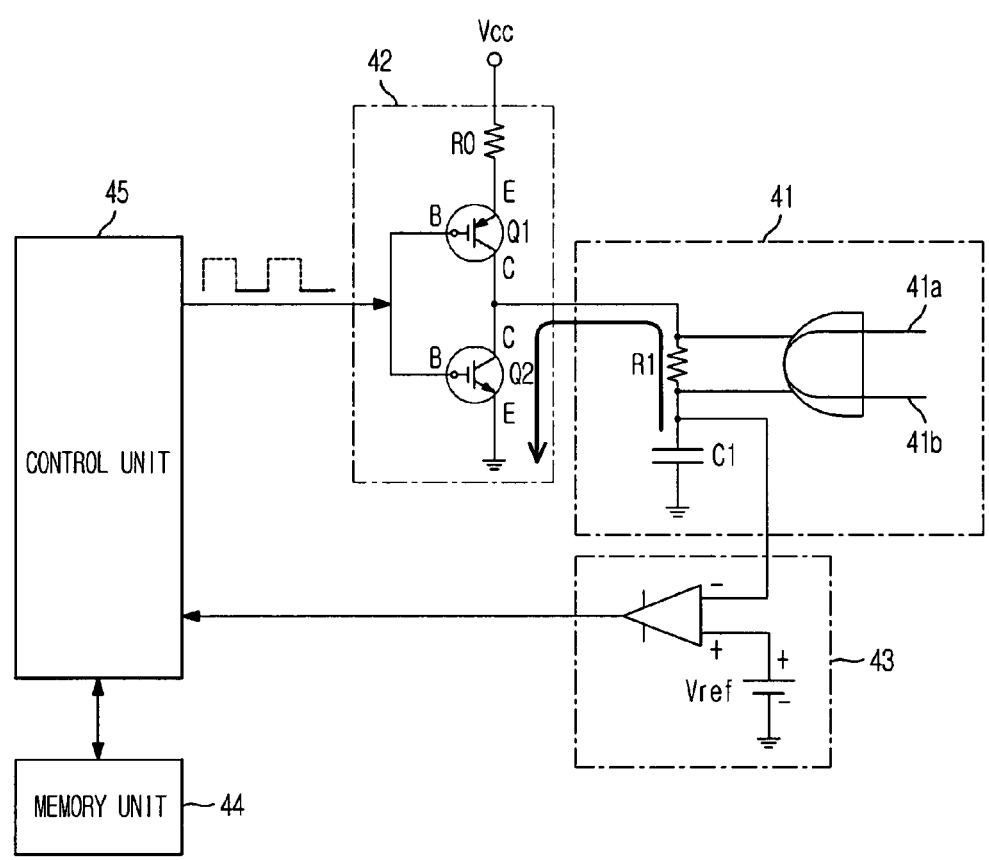
FIG. 6 is a diagram showing a state in which the capacitor is discharged through the measuring electrodes of the salinity sensing unit shown in FIG. 3.
Figure 7:
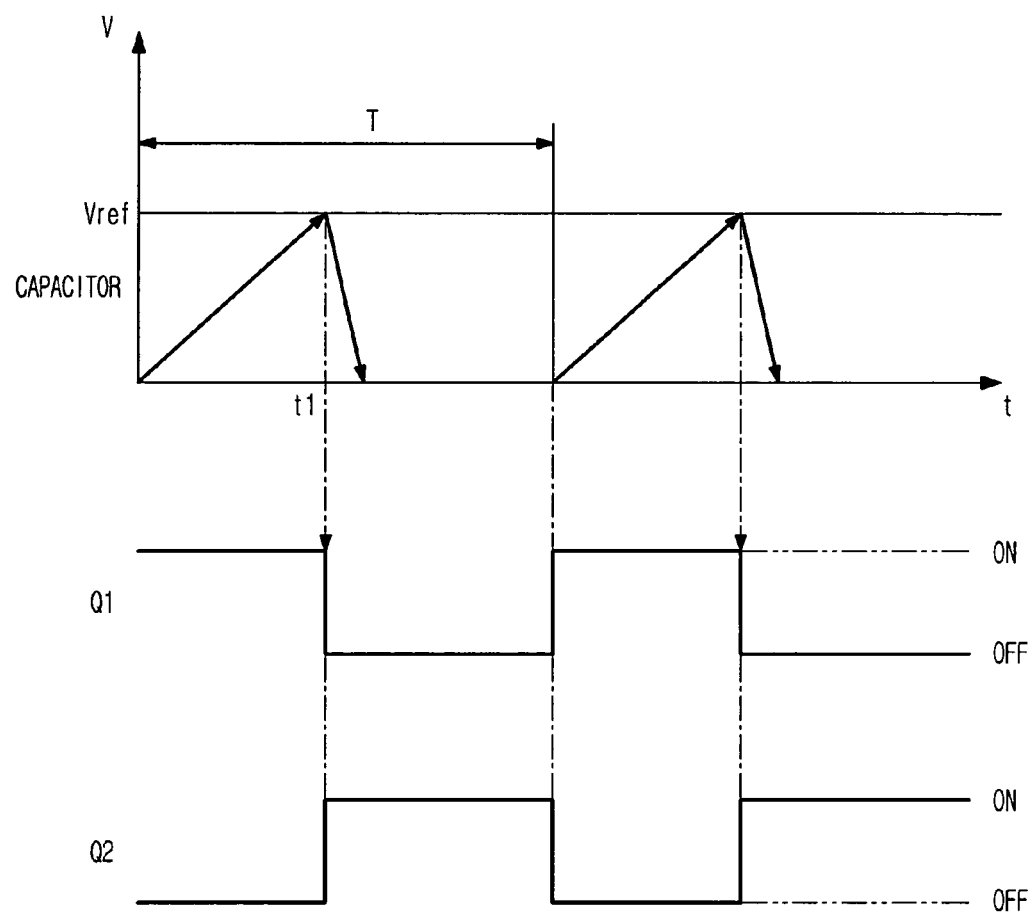
FIG. 7 is a timing chart illustrating the voltage of the capacitor according to an operation of a switching unit in the salinity measuring apparatus according to the embodiment.

FIG. 4 is a diagram showing a state in which a voltage is applied to a capacitor through the measuring electrodes of the salinity sensing unit shown in FIG. 3 so as to charge the capacitor. FIG. 5 is a timing chart illustrating a variation in time when the voltage of the capacitor reaches a reference voltage according to a salinity variation and a variation in duty ratio of a Pulse Width Modulation (PWM) signal, in the salinity measuring apparatus according to the embodiment. FIG. 6 is a diagram showing a state in which the capacitor is discharged through the measuring electrodes of the salinity sensing unit shown in FIG. 3. FIG. 7 is a timing chart illustrating the voltage of the capacitor according to an operation of a switching unit in the salinity measuring apparatus according to the embodiment.

As shown in FIG. 4, the control unit 45 switches the first switching element Q1 of the switching unit 42 on and switches the second switching element Q2 off during an on time period (see a solid line of the PWM signal) of the PWM signal output to the switching unit 42 (see FIG. 7). Accordingly, current flows in an arrow direction so as to charge the capacitor C1.

As shown in FIG. 5, the charging time of the capacitor C1 is changed according to salinity.

Accordingly, the time when the voltage of the capacitor C1 reaches the reference voltage Vref is changed according to salinity. That is, when salinity is high, the time when the voltage A (solid arrow) of the capacitor C1 reaches the reference voltage Vref is "t1". In contrast, when salinity is low, since the conductivity between the measuring electrodes 41a and 41b is relatively low, the time when the voltage B (dotted arrow) of the capacitor C1 reaches the reference voltage Vref is "t2" greater than "t1".

Accordingly, the time when the voltage of the capacitor C1 reaches the reference voltage is changed according to a salinity variation. That is, as the salinity is increased, the time when the voltage A of the capacitor C1 reaches the reference voltage Vref is decreased (t1<t2).

By respectively converting the times "t1" and "t2" required to charge the capacitor up to the reference voltage Vref into the duty ratios C and D of the pulse signal output to the switching unit 42, it is possible to estimate and measure salinity. At this time, since the period T of each pulse signal is identical and only the duty ratio of the pulse signal is changed according to the salinity variation, it is possible to determine salinity based on the duty ratio.

As shown in FIG. 6, the control unit 45 switches the first switching element Q1 of the switching unit 42 off and switches the second switching element Q2 on during an off time period (see a solid line of the PWM signal) of the PWM signal output to the switching unit 42 (see FIG. 7). Accordingly, current flows in an arrow direction so as to discharge the capacitor C1.

Figure 8:
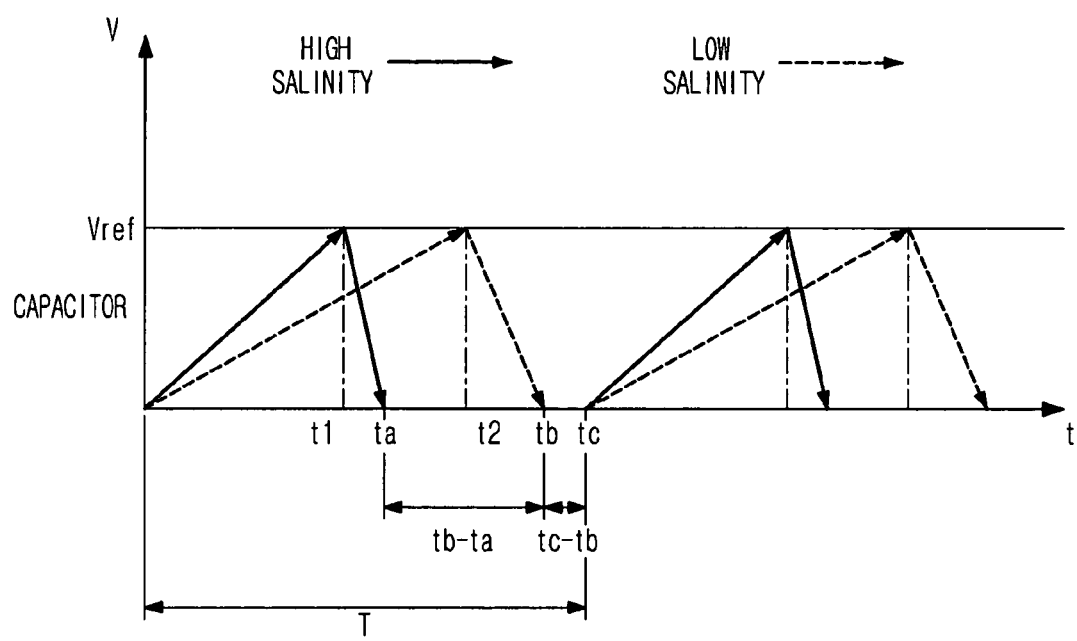
FIG. 8 is a diagram illustrating a period when the voltage of the capacitor is substantially 0 when the capacitor is discharged, in the salinity measuring apparatus according to the embodiment.

FIG. 8 is a diagram illustrating the existence of a period when the voltage of the capacitor is substantially 0 when the capacitor is discharged, in the salinity measuring apparatus according to the embodiment.

As shown in FIG. 8, since periods tb–ta and tc–tb when the voltage of the capacitor C1 is substantially 0 when the capacitor C1 is discharged are present within one period T, ions accumulated in the measuring electrodes 41a and 41b are discharged and the ions accumulated in the measuring electrodes 41a and 41b are minimized.

Figure 9:
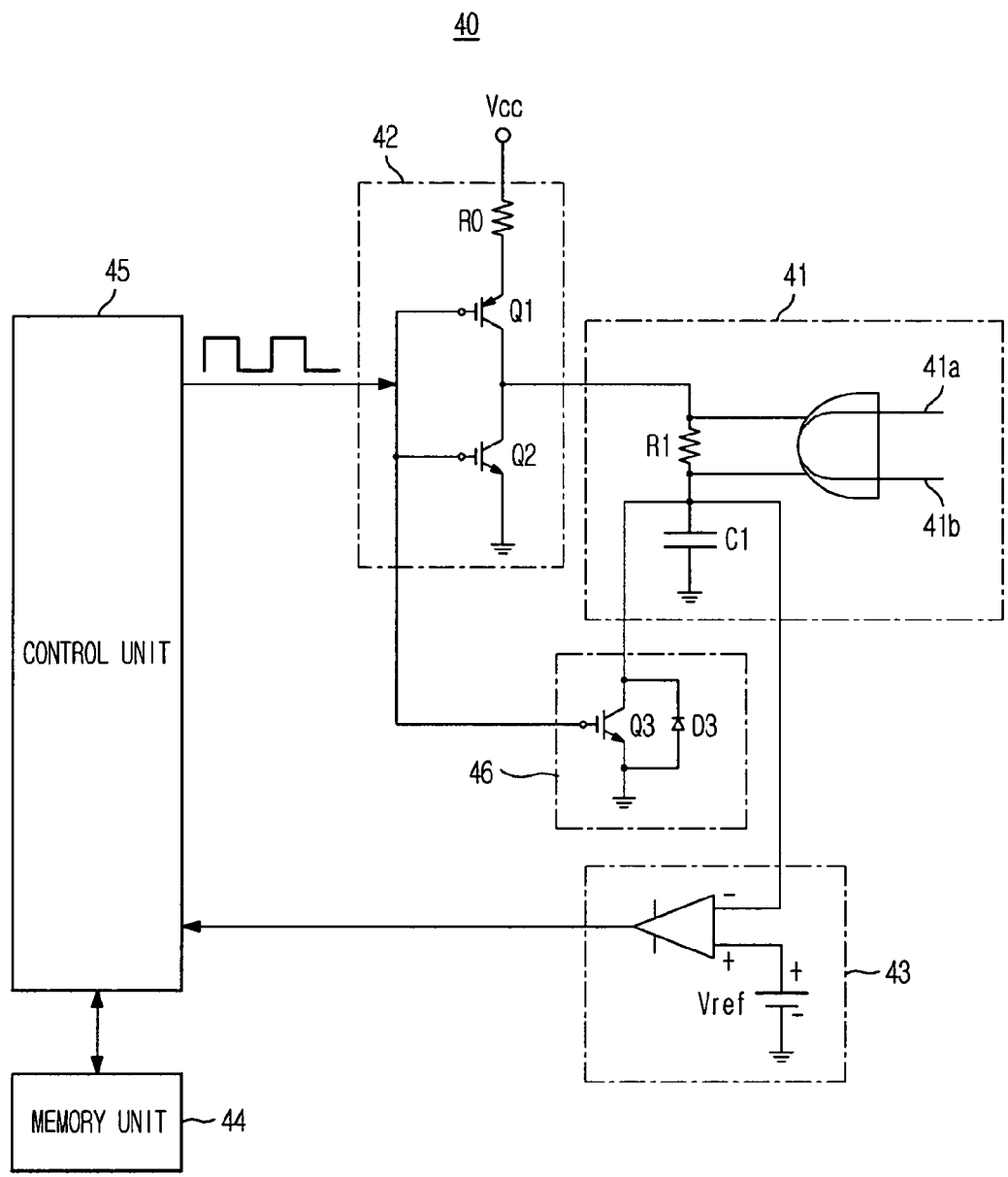
FIG. 9 is a block diagram of a salinity measuring apparatus according to another embodiment.

FIG. 9 is a block diagram of a salinity measuring apparatus according to another embodiment.

As shown in FIG. 9, the salinity measuring apparatus according to another embodiment may include a discharging unit 46 to effectively discharge the capacitor C1 of the salinity sensing unit 41.

The discharging unit 46 is provided between the salinity sensing unit 41 and the switching unit 42.

The discharging unit 46 includes a freewheeling diode D3 and a third switching element Q3. The collector C of the third switching element Q3 is connected to one side of the capacitor C1 of the salinity sensing unit 41 and the emitter thereof is connected to the ground side. In addition, the bases B of the third switching element Q3 and the second switching element Q2 are connected to each other such that the operation of the third switching element Q3 interlocks with the operation of the second switching element Q2.

Accordingly, since the third switching element Q3 of the discharging unit 46 is switched on when the second switching element Q2 of the switching unit 42 is switched on, it is possible to rapidly and completely discharge the capacitor C1.

Due to the fast capacitor discharge, the periods tb–ta and tc–tb when the voltage of the capacitor is substantially 0 may be increased and more easily secured. Thus, it is possible to further reduce ions accumulated in the measuring electrodes 41a and 41b.

Figure 10:
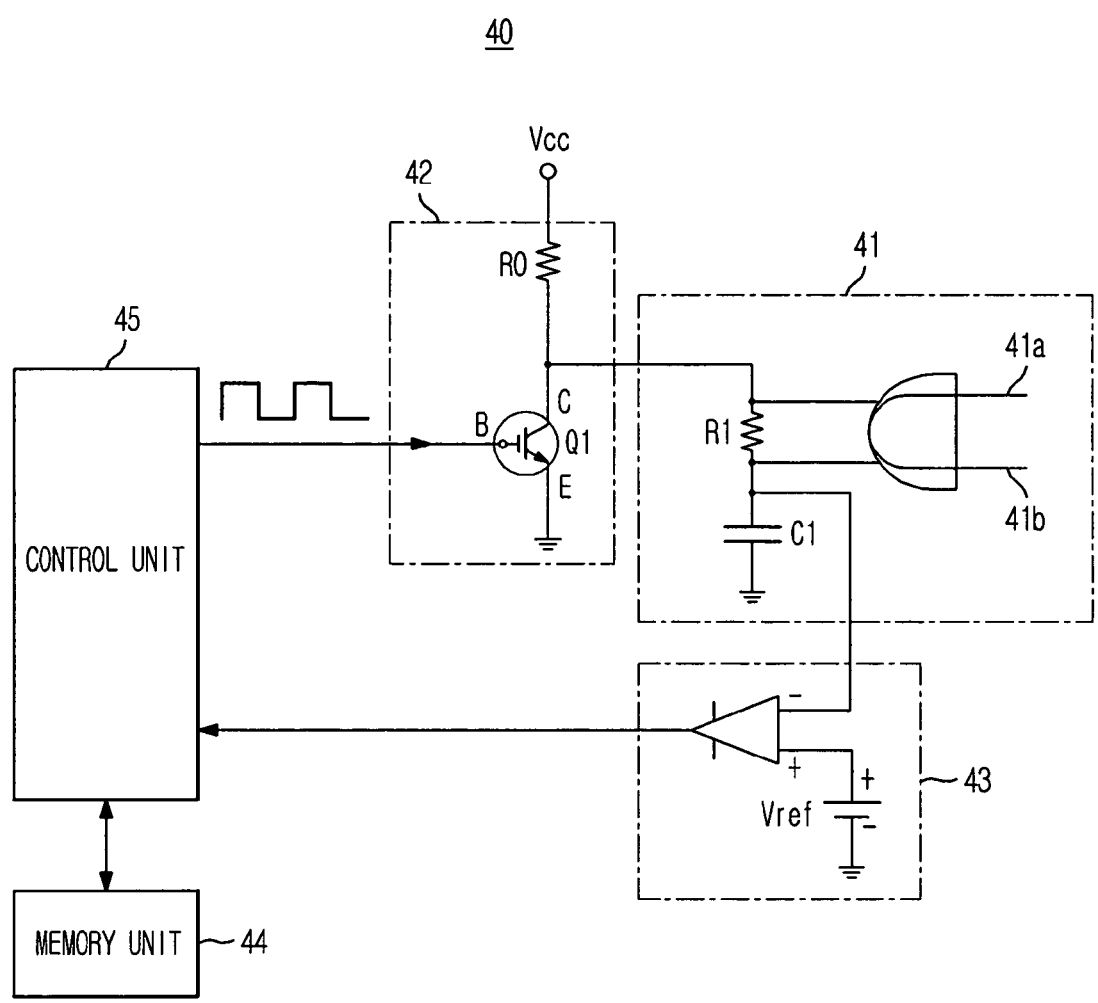
FIG. 10 is a block diagram of a salinity measuring apparatus according to another embodiment.

FIG. 10 is a block diagram of a salinity measuring apparatus according to another embodiment.

In the salinity measuring apparatus shown in FIG. 10, one switching element is used instead of the two switching elements in the switching unit 42 of the salinity measuring apparatus shown in FIG. 3.

As shown in FIG. 10, the salinity measuring apparatus according to another embodiment includes a salinity sensing unit 41, a switching unit 42 including one switching element Q1, a comparison unit 43, a memory unit 44 and a control unit 45 to perform overall control.

The salinity sensing unit 41 includes a first electrode 41a and a second electrode 41b spaced apart from the first electrode 41a with a predetermined gap therebetween so as not to be in contact with the first electrode 41a, and includes the pair of measuring electrodes 41a and 41b provided to be in contact with the liquid of the food stored in the storage chamber, the resistor R1 and the capacitor C1 connected to the second electrode 41b of the measuring electrodes 41a and 41b in series.

The switching unit 42 supplies a voltage to the salinity sensing unit 41 according to a PWM signal with a constant frequency, which is output from the control unit 45, so as to charge the capacitor C1 or to discharge the capacitor C1 to a ground side. For example, the switching unit 42 includes one transistor Q1. The transistor is an NPN transistor Q1.

If the switching element Q1 is switched off, the voltage is supplied to the salinity sensing unit 41 so as to charge the capacitor C1. In contrast, if the switching element Q1 is switched on, the capacitor C1 of the salinity sensing unit 41 is discharged.

The comparison unit 43 compares the voltage of the capacitor C1 of the salinity sensing unit 41 with a predetermined reference voltage Vref and outputs a high-level signal or a low-level signal to the control unit 45 according to the comparison result. For example, the comparison unit 43 outputs a high-level signal if the input voltage value is less than the reference voltage Vref and outputs a low-level signal if the input voltage value is higher than the reference voltage Vref.

The control unit 45 outputs the pulse signal (PWM signal) with the constant frequency to the switching unit 42 such that an AC voltage is supplied to the salinity sensing unit 41 and switches the switching element Q1 of the switching unit 42 off. Then, the capacitor C1 of the salinity sensing unit 41 is charged.

When the signal received from the comparison unit 42 is changed from the low-level signal to the high-level signal, the control unit 45 controls the PWM signal output to the switching unit 42 such that the capacitor C1 of the salinity sensing unit 41 is discharged and switches the switching element Q1 of the switching unit 41 on. Then, the capacitor C1 of the salinity sensing unit 41 is discharged.

Meanwhile, the control unit 45 determines the salinity of the food which is in contact with the measuring electrodes 41a and 41b of the salinity sensing unit 41 based on when the voltage of the capacitor C1 reaches the reference voltage.

Salinity-time data is stored in the memory unit 44. The time values changed according to the salinity of the standard food measured by experiments are stored in the memory unit 44.

At this time, the time when the voltage of the capacitor C1 reaches the reference voltage is a time when the first switching element Q1 is switched off to a time when the first switching element Q1 is switched on, which corresponds to the duty ratio of the PWM signal. Thus, the control unit 45 may determine the salinity of the food by checking the duty ratio of the PWM signal. In this case, salinity-duty ratio data is stored in the memory unit 44.

Figure 11:
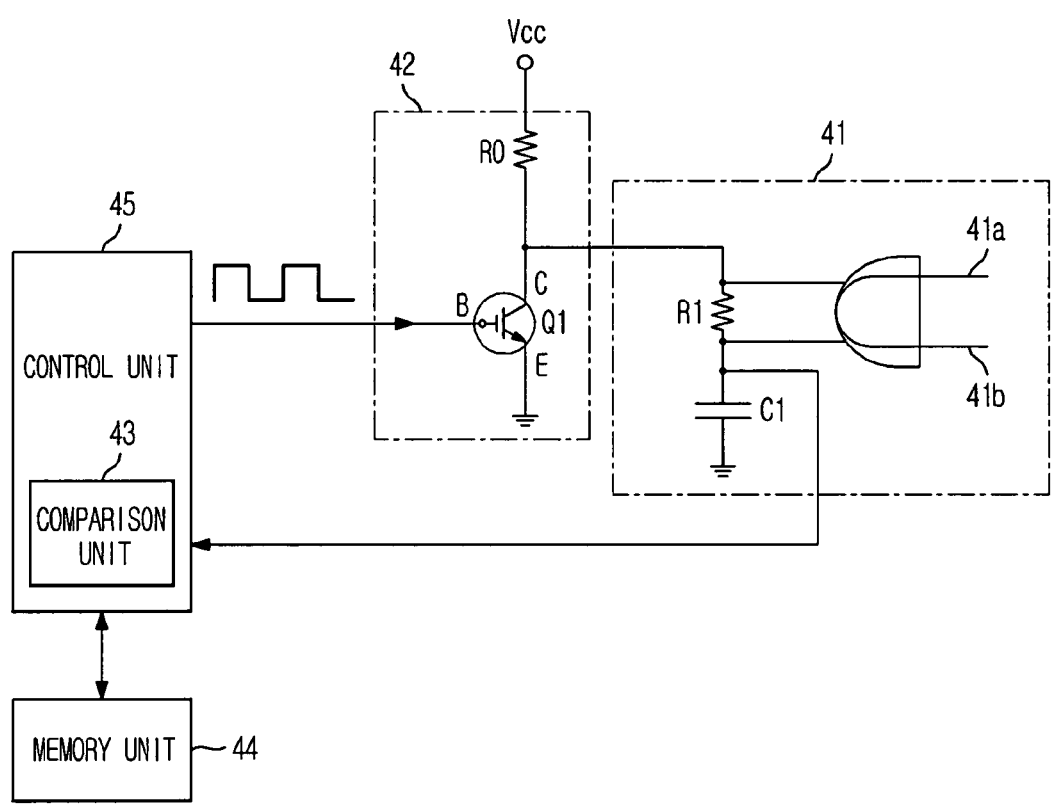
FIG. 11 is a block diagram of a salinity measuring apparatus according to another embodiment.

FIG. 11 is a block diagram of a salinity measuring apparatus according to another embodiment.

In the salinity measuring apparatus shown in FIG. 11, the function of the comparison unit 43 of the salinity measuring apparatus shown in FIG. 9 is incorporated into the control unit 45.

As shown in FIG. 11, the salinity measuring apparatus according to another embodiment includes a salinity sensing unit 41, a switching unit 42 including one switching element Q1, a memory unit 44 and a control unit 45 including a comparison unit 43.

The salinity sensing unit 41 includes a first electrode 41a and a second electrode 41b spaced apart from the first electrode 41a with a predetermined gap therebetween so as not to be in contact with the first electrode 41a, and includes the pair of measuring electrodes 41a and 41b provided to be in contact with the liquid of the food stored in the storage chamber, the resistor R1 and the capacitor C1 connected to the second electrode 41b of the measuring electrodes 41a and 41b in series.

The switching unit 42 supplies a voltage to the salinity sensing unit 41 according to a PWM signal with a constant frequency, which is output from the control unit 45, so as to charge the capacitor C1 or to discharge the capacitor C1 to a ground side. For example, the switching unit 42 includes one transistor Q1. The transistor is an NPN transistor Q1.

If the switching element Q1 is switched off, the voltage is supplied to the salinity sensing unit 41 so as to charge the capacitor C1. In contrast, if the switching element Q1 is switched on, the capacitor C1 of the salinity sensing unit 41 is discharged.

The control unit 45 outputs the pulse signal (e.g., PWM signal) with the constant frequency to the switching unit 42 such that an AC voltage is supplied to the salinity sensing unit 41 and switches the switching element Q1 of the switching unit 42 off. Then, the capacitor C1 of the salinity sensing unit 41 is charged.

In addition, the control unit 45 determines whether the voltage of the capacitor C1 of the salinity sensing unit 41 is higher or lower than the reference voltage Vref, from the output signal of the comparison unit 43. At this time, when the output signal of the comparison unit 43 is changed from the high-level signal to the low-level signal, the control unit 45 determines that the voltage of the capacitor C1 reaches the reference voltage Vref.

In addition, the control unit 45 determines the salinity of the food which is in contact with the measuring electrodes 41a and 41b of the salinity sensing unit 41 based on a time when the voltage of the capacitor C1 reaches the reference voltage.

At this time, the time when the voltage of the capacitor C1 reaches the reference voltage is a time when the first switching element Q1 is switched off to a time when the first switching element Q1 is switched on, which corresponds to the duty ratio of the PWM signal. Thus, the control unit 45 may determine the salinity of the food by checking the duty ratio of the PWM signal. In this case, salinity-duty ratio data is stored in the memory unit 44.

Figure 12:
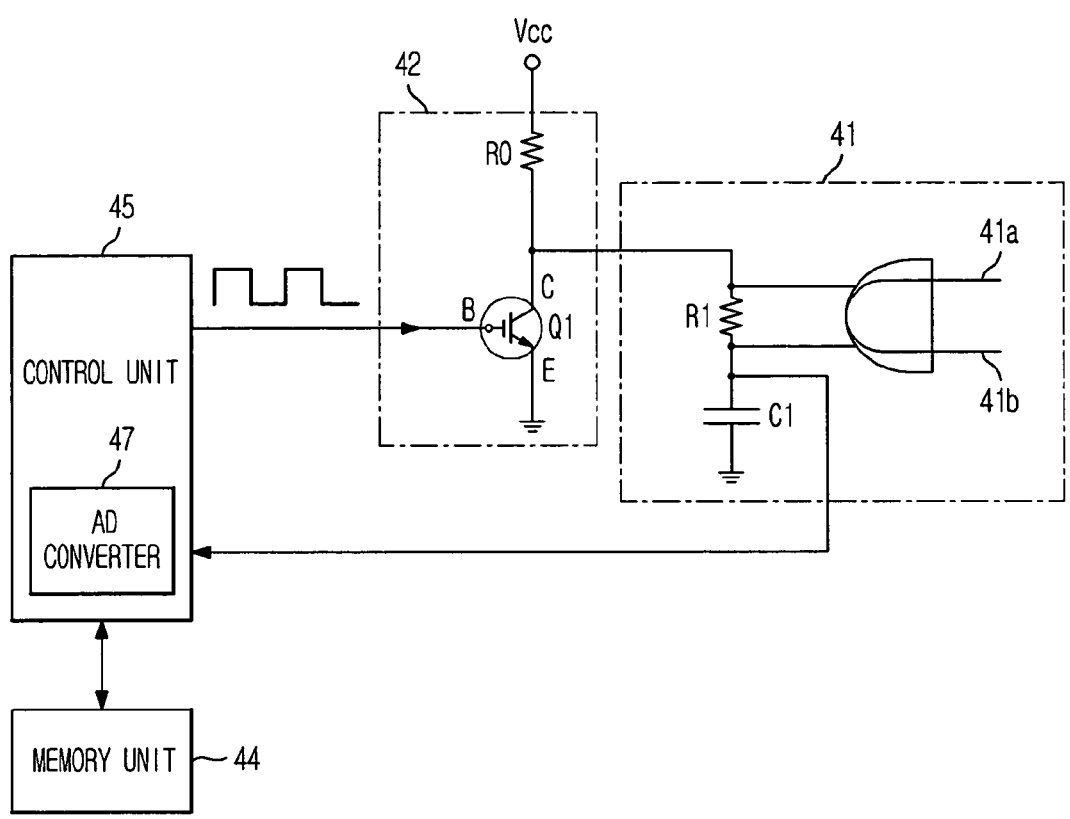
FIG. 12 is a block diagram of a salinity measuring apparatus according to another embodiment.

FIG. 12 is a block diagram of a salinity measuring apparatus according to another embodiment.

As shown in FIG. 12, in the salinity measuring apparatus according to another embodiment, the control unit 45 includes an AD converter 47 to convert an analog signal into a digital signal, instead of the comparison unit 43.

As shown in FIG. 12, the salinity measuring apparatus according to another embodiment of the present invention includes a salinity sensing unit 41, a switching unit 42, a memory unit 44, an AD converter 47, and a control unit 45 to perform overall control.

The control unit 45 may include the AD converter 47.

The AD converter 47 is connected to the capacitor C1 of the salinity sensing unit 41 so as to convert the analog voltage signal of the capacitor C1 into a digital signal and to output the digital signal to the control unit 45.

The control unit 45 recognizes the voltage of the capacitor C1 from the digital signal input through the AD converter 47 and counts the time when the recognized capacitor voltage reaches the reference voltage Vref so as to determine the time when the voltage of the capacitor reaches the reference voltage Vref.

As described above, the control unit 45 determines the salinity of the food which is in contact with the measuring electrodes 41a and 41b of the salinity sensing unit 41 based on the time when the voltage of the capacitor C1 reaches the reference voltage.

At this time, the time when the voltage of the capacitor C1 reaches the reference voltage corresponds to a time when the first switching element Q1 is switched off to a time when the first switching element Q1 is switched on, which corresponds to the duty ratio of the PWM signal. Thus, the control unit 45 may determine the salinity of the food by checking the duty ratio of the PWM signal. In this case, salinity-duty ratio data is stored in the memory unit 44.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A salinity measuring apparatus to determine salinity of food, the salinity measuring apparatus comprising:
   a salinity sensing unit including a pair of measuring electrodes, a capacitor, and a resistor, the resistor being connected between the measuring electrodes in parallel;
   a switching unit to switch a voltage of the capacitor of the salinity sensing unit; and
   a control unit to provide a pulse signal with a constant frequency to the switching unit and to determine the salinity of the food which is in contact with the measuring electrodes of the salinity sensing unit based on a time when the voltage of the capacitor reaches a reference voltage, wherein the period of the pulse signal includes a period when the voltage of the capacitor is substantially 0 when the capacitor is discharged.

2. The salinity measuring apparatus according to claim 1, wherein, in the salinity sensing unit, the capacitor is connected to any one of the measuring electrodes in series.

3. The salinity measuring apparatus according to claim 1, further comprising a memory unit to store a salinity value changed according to a time when the voltage of the capacitor reaches the reference voltage.

4. The salinity measuring apparatus according to claim 1, further comprising a comparison unit to compare the voltage of the capacitor of the salinity sensing unit with the reference voltage and to output a high-level signal or a low-level signal according to the comparison result,
wherein the control unit determines a time when the voltage of the capacitor reaches the reference voltage based on a variation in output signal of the comparison unit.

5. The salinity measuring apparatus according to claim 1, further comprising an AD converter connected to the capacitor so as to convert an analog voltage signal of the capacitor into a digital signal,
wherein the time when the voltage of the capacitor reaches the reference voltage is determined according to the digital signal converted by the AD converter.

6. The salinity measuring apparatus according to claim 4, wherein the control unit controls the switching unit such that the capacitor is discharged when the voltage of the capacitor reaches the reference voltage.

7. The salinity measuring apparatus according to claim 5, wherein the control unit controls the switching unit such that the capacitor is discharged when the voltage of the capacitor reaches the reference voltage.

8. The salinity measuring apparatus according to claim 1, further comprising a discharging unit connected to one side of the capacitor of the salinity sensing unit to discharge the capacitor.

9. The salinity measuring apparatus according to claim 8, wherein the operation of the discharging unit interlocks with a discharging operation of the switching unit.

10. A salinity measuring apparatus comprising:
a salinity sensing unit including a pair of measuring electrodes, a capacitor, and a resistor, the resistor being connected between the measuring electrodes in parallel;
a switching unit to switch a voltage of the capacitor of the salinity sensing unit; and
a control unit to provide a pulse signal with a constant frequency to the switching unit, to determine a duty ratio of the pulse signal when the voltage of the capacitor reaches the reference voltage, and to determine salinity of food which is in contact with the measuring electrodes of the salinity sensing unit according to the determined duty ratio,
wherein the period of the pulse signal includes a period when the voltage of the capacitor is substantially 0 when the capacitor is discharged.

11. The salinity measuring apparatus according to claim 10, further comprising a memory unit to store a salinity value corresponding to the duty ratio.

12. The salinity measuring apparatus according to claim 10, further comprising a comparison unit to compare the voltage of the capacitor of the salinity sensing unit with the reference voltage and to output a high-level signal or a low-level signal according to the comparison result,
wherein the control unit determines a time from when the pulse signal is output to the switching unit to when the output signal of the comparison unit is changed, as the duty ratio of the pulse signal.

13. The salinity measuring apparatus according to claim 10, wherein the control unit controls the switching unit such that the capacitor is discharged when the voltage of the capacitor reaches the reference voltage.

14. The salinity measuring apparatus according to claim 10, further comprising a discharging unit connected to one side of the capacitor of the salinity sensing unit to discharge the capacitor.

15. The salinity measuring apparatus according to claim 14, wherein the operation of the discharging unit interlocks with a discharging operation of the switching unit.

16. A salinity measuring apparatus comprising:
a salinity sensing unit including a pair of measuring electrodes, a capacitor, and a resistor, the resistor being connected between the measuring electrodes in parallel;
a switching unit switched to charge or discharge the capacitor of the salinity sensing unit; and
a control unit to provide a pulse signal with a constant frequency to the switching unit, to control the switching unit so as to charge the capacitor and to control the switching unit so as to discharge the capacitor when the voltage of the capacitor reaches a reference voltage,
wherein the period of the pulse signal includes a period when the voltage of the capacitor is substantially 0 when the capacitor is discharged.

17. The salinity measuring apparatus according to claim 16, further comprising a comparison unit to compare the voltage of the capacitor of the salinity sensing unit with the reference voltage and to output a high-level signal or a low-level signal according to the comparison result,
wherein the control unit determines whether or not the voltage of the capacitor reaches the reference voltage based on a variation in output signal of the comparison unit.

18. A salinity measuring apparatus comprising:
a salinity sensing unit including a pair of measuring electrodes, a capacitor, and a resistor, the resistor being connected between the measuring electrodes in parallel;
a switching unit to switch a voltage applied to the salinity sensing unit; and
a control unit to provide a pulse signal with a constant frequency to the switching unit, to change a duty ratio of the pulse signal based on a time when the voltage of the capacitor reaches a reference voltage, and to determine salinity of food which is in contact with the measuring electrodes of the salinity sensing unit,
wherein the period of the pulse signal includes a period when the voltage of the capacitor is substantially 0 when the capacitor is discharged.

* * * * *